(12) United States Patent
Tokudome et al.

(10) Patent No.: US 7,089,053 B1
(45) Date of Patent: Aug. 8, 2006

(54) COMPOSITIONS FOR DRUG ADMINISTRATION BY ELECTROPORATION

(75) Inventors: Yoshihiro Tokudome, Yokohama (JP); Koji Owaku, Yokohama (JP); Kenichi Goto, Yokohama (JP); Kenji Sugibayashi, Kawagoe (JP)

(73) Assignee: Pola Chemical Industries Inc, Shizuoka (JP)

( * ) Notice: Subject to any disclaimer, the term of this patent is extended or adjusted under 35 U.S.C. 154(b) by 0 days.

(21) Appl. No.: 10/110,590

(22) PCT Filed: Apr. 6, 2000

(86) PCT No.: PCT/JP00/02242

§ 371 (c)(1),
(2), (4) Date: Apr. 11, 2002

(87) PCT Pub. No.: WO01/26689

PCT Pub. Date: Apr. 19, 2001

(30) Foreign Application Priority Data

Oct. 14, 1999 (JP) .................................. 11-291721

(51) Int. Cl.
*A61N 1/30* (2006.01)
*A61K 9/08* (2006.01)
*A61K 9/10* (2006.01)

(52) U.S. Cl. .................... 604/20; 424/400; 514/329

(58) Field of Classification Search ............... 604/20; 435/4, 287.1, 288.4; 514/253.04, 259.41, 514/329, 946, 446, 447; 424/448–449; 607/3
See application file for complete search history.

(56) References Cited

U.S. PATENT DOCUMENTS

| 4,933,184 | A | 6/1990 | Tsuk |
| 5,069,908 | A | 12/1991 | Henley |
| 5,990,179 | A | 11/1999 | Gyory et al. |
| 5,997,501 | A | 12/1999 | Gross et al. |
| 6,248,349 | B1 | 6/2001 | Suzuki et al. |
| 6,266,560 | B1 * | 7/2001 | Zhang et al. ............ 604/20 |
| 6,527,759 | B1 | 3/2003 | Tachibana et al. |
| 6,678,558 | B1 * | 1/2004 | Dimmer et al. ........... 607/3 |
| 6,743,432 | B1 | 6/2004 | Yanai et al. |
| 2001/0008896 | A1 * | 7/2001 | Smith et al. |

FOREIGN PATENT DOCUMENTS

| EP | 0 480 054 A1 | 10/1991 |
| GB | 2 239 600 | 7/1991 |
| GB | 2 239 600 A | 7/1991 |
| JP | 02-000468 | 1/1990 |
| JP | 06016538 | 1/1994 |
| JP | 09-255561 | 9/1997 |
| WO | WO 89/06555 | 7/1989 |
| WO | WO 96/00111 | 1/1996 |
| WO | WO 00/23099 | 4/2000 |

OTHER PUBLICATIONS

Supplementary European Search Report completed Feb. 3, 2005 and issued to a related foreign application.

* cited by examiner

*Primary Examiner*—Kevin C. Sirmons
*Assistant Examiner*—Roz Maiorino
(74) *Attorney, Agent, or Firm*—Knobbe, Martens, Olson & Bear LLP

(57) ABSTRACT

The present invention relates to compositions for electroporation which are useful in elevating a percutaneous absorbability of drugs, etc. By adding polyhydric alcohols to compositions for electroporation, the percutaneous absorbability of drugs is elevated.

4 Claims, 1 Drawing Sheet

COMPOSITIONS FOR DRUG ADMINISTRATION BY ELECTROPORATION

CROSS-REFERENCE TO RELATED APPLICATIONS

This is the National Phase under 35 U.S.C. § 371 of International Application No. PCT/JP00/02242, filed Apr. 6, 2000, which claims priority to Japanese Patent Application No. 11/291721 filed Oct. 14, 1999. The International Application was published under PCT Article 21(2) in a language other than English.

BACKGROUND OF THE INVENTION

1. Field of the Invention

The present invention relates to compositions for electroporation which are useful for elevating a percutaneous absorbability of drugs, etc. The present invention is useful in the field of drugs.

2. Description of the Related Art

Although percutaneous absorption route has been expected as an administration route for drugs since it gives less pain than injection does and in addition it involves less possibility of forgetting to administrate drugs than oral administration does, it is rather difficult to allow percutaneous absorption due to a preventive function that the skin inherently has so that under the present circumstances the percutaneous absorption route has not been established yet as means for delivering drugs. As one devised method in order to overcome the present problem, a so-called electroporation may be exemplified according to which pores are formed in the skin structure by application of a voltage and a drug is delivered through such pores. Recently, it has become clear that in such an electroporation, the behavior of drugs is different from that in ordinary administration so that it has been desired to develop compositions for percutaneous administration which are suitable for such an electroporation.

On the other hand, no composition for electroporation that comprises polyhydric alcohol or monoterpene has been known at all or it has been unknown that compositions comprising such polyhydric alcohol or monoterpene have excellent percutaneous absorption promoting effects.

SUMMARY OF THE INVENTION

The present invention has been made under the aforementioned circumstances and is aimed at providing a composition for percutaneous administration which is suitable for electroporation.

In consideration of such circumstances, the present inventors have made extensive studies in pursuit of a composition for percutaneous administration which is suitable for electroporation. As a result the inventors have found that a composition comprising polyhydric alcohol and preferably further comprising monoterpenes is preferable as a composition for percutaneous administration which is suitable for electroporation, thus achieving the present invention. That is, the present invention provides a composition for electroporation that comprises polyhydric alcohol. Furthermore, the present invention provides a polyhydric alcohol-comprising composition for electroporation that preferably comprises monoterpene.

The composition for electroporation of the present invention comprises polyhydric alcohol. As the polyhydric alcohol that can be used for the composition for electroporation of the present invention, any polyhydric alcohol can be used without any particular limitation as far as it is usually used in similar fields such as skin external agents. Preferred examples thereof include polyethylene glycol, 1,3-butanediol, propylene glycol, glycerol, dipropylene glycol, diglycerol, sorbitol, maltitol and the like. Among these, one or more selected from propylene glycol, glycerol, polyethylene glycol and 1,3-butanediol are preferred. It is preferred that they are in a state of liquid at 25° C. and at 1 atm and have a molecular weight on the order of 80 to 200. This is because such conditions allow elevation of percutaneous absorbability in electroporation. Among these, a more preferred one is propylene glycol. It is particularly preferred that the polyhydric alcohol consists of only this one. This is because it is a component excellent in elevating particularly percutaneous absorbability in electroporation and at the same time it has many utilization track records as skin external agents and its properties on safety have already been grasped. In the composition for electroporation of the present invention, a preferred content of the polyhydric alcohol is 1 to 90% by weight and more preferably 5 to 30% by weight. This value has been set up in consideration of safety of the polyhydric alcohol, degree of freedom in selecting optional components in preparation forms of the composition, effective dose of the active ingredients, and optimal amount for percutaneous absorption promoting effect.

The composition for electroporation of the present invention in a preferred embodiment further comprises monoterpene. Examples of the monoterpene include menthol and its optical isomers, menthone, thymol, etc. Among these, menthol is preferred and l-menthol is more preferred. This is because, among the monoterpenes, menthols, in particular l-menthol are excellent particularly in the percutaneous absorption promoting effect in electroporation of the present invention. In the composition for electroporation of the present invention, a preferred content of monoterpenes is 0.1 to 10% by weight and more preferably 0.5 to 5% by weight. This is because, if the monoterpenes are present too much, they cause irritation in some cases and if they are present too little, no percutaneous absorbability promoting effect can be obtained in some cases.

The compositions for electroporation of the present invention may comprise optional components for manufacturing pharmaceutical preparations which are used for ordinary compositions for electroporation in addition to the polyhydric alcohol, which is an essential component, and the monoterpenes, which are preferred components. Preferred examples of such optional components include, for example, hydrocarbons such as squalene, vaseline, microcrystalline wax, esters such as jojoba oil, carnauba wax, and octyldodecyl oleic acid, triglycerides such as olive oil, beef tallow, and coconut oil, fatty acids such as stearic acid, oleic acid and ricinoleic acid, higher alcohols such as oleyl alcohol, stearyl alcohol, and octyldodecanol, anionic surfactants such as sulfosuccinic acid esters and sodium polyoxyethylenealkylsulfates, amphoteric surfactants such as alkylbetaine salts, cationic surfactants such as dialkylammonium salts, nonionic surfactants such as sorbitan fatty acid esters, fatty acid monoglycerides, polyoxyethylene adducts of these, polyoxyethylene alkyl ethers and polyoxyethylene fatty acid esters, viscosity bodying and gelling agents, antioxidants, ultraviolet absorbents, coloring agents, preservatives, powders and the like. Further, as drugs that are to be percutaneously administered by such an electroporation, those usually used as medical preparations can be applied without any particular limitation. For example, analgesic antipyretic anti-inflammatory agents such as codeine, morphine, hydromorphone, oxycodone, pethidine, buprenorphin hydrochloride, pentazocine, and tramadol hydrochloride, protein-based drugs such as insulin, carcitonin, elcatonin, adrenocorticotrophic hormone (ACTH), parathyroid hormone (PTH), selectin, oxytocin, angiotensin, β-endorphin, vasopressin, glucagon, somatostatin, luteinizing hormone-releasing hormone (LH-RH), enkephalin, neurotensin, atrial sodium diuretic peptide (ANP), growth hormone, bradykinin, substance P, dynorphin, thyroid stimulating hormone (TSH), prolactin, G-CSF, glutathione peroxidase, superoxide dismutase (SOD), desmopressin, somatomedin, melanocyte stimulating hormone (MSH), calcitonin gene related peptide (CGRP), endothelin, and thyrotropin releasing hormone (TRH), interleukins, interferons, anti-platelet drugs, vasodilaters, argatroban as anti-arteriosclerotic drug, sarpogrelate hydrochloride, sodium beraprost, limaprost alfadex, and cilostazol and the like. These drugs must be administered with passage of time by necessary amounts so that they are agreeable to the properties of percutaneous administration. The compositions for electroporation of the present invention are processed into preparation forms in conformity with the physical properties or the like of the active ingredients, such as solutions, emulsions, semi-solids, and solids, by treating the aforementioned essential components, preferred components, optional components and active ingredients, and are used in electroporation. That is, by using the compositions of the present invention, drugs as active ingredients can be percutaneously administered by electroporation. Upon electroporation, they are used together with a device for electroporation. Among the aforementioned preparation forms, preferred preparation forms include aqueous preparation forms and particularly preferred are an aqueous solution preparation form, aqueous gel preparation form and emulsion preparation form.

The unit for administrating drugs for external application to the skin of the present invention includes the composition for electroporation and a device for electroporation of the present invention in combination. The device for electroporation is not particularly limited as far as it is used usually in such a use, and for example, those devices described in Japanese Domestic Patent Laid Open Publication No. Hei 11-507341 (laying open of a Japanese translation), Japanese Domestic Patent Laid Open Publication No. Hei 11-505445 (laying open of a Japanese translation), Japanese Domestic Patent Laid Open Publication No. Hei 10-502827 (laying open of a Japanese translation), Japanese Domestic Patent Laid Open Publication No. Hei 11-503349 (laying open of a Japanese translation), Japanese Domestic Patent Laid Open Publication No. Hei 08-511680 (laying open of a Japanese translation), Japanese Domestic Patent Laid Open Publication No. Hei 03-502416 (laying open of a Japanese translation), etc. may be used. Further, those commercially available devices for such an electroporation include ECM-600 produced by BTX Co., GENE PULSER produced by BIO-RAD Co., etc. Also, these may be used. As for the conditions of electroporation, it is preferred to impress electric current for about 30 seconds with the voltage set to about 300 V and the capacitance of capacitor set to about 25 μF.

BEST MODE FOR CARRYING OUT THE INVENTION

Figure 1:
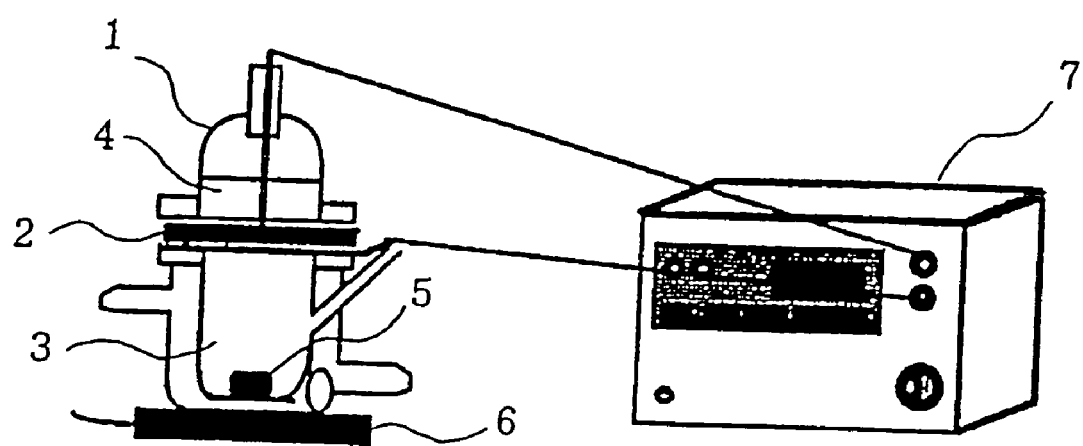
FIG. 1 is a diagram showing the apparatus for electroporation used in Example 3.

Hereinafter, the present invention will be described in more detail by way of examples. Of course, the present invention is not limited to the examples.

EXAMPLES 1 AND 2

According to the recipes shown in Table 1, compositions for electroporation of the present invention were prepared. As a model labeled drug, 1 mM sodium calcein was used. These were stirred and solubilized to prepare compositions (liquid agents) for electroporation of the present invention.

TABLE 1

| Composition | Example 1 | Example 2 |
|---|---|---|
| Physiological saline sodium calcein | 50 parts by weight (1 mM; final concentration) | 47 parts by weight (1 mM; final concentration) |
| Propylene glycol | 50 parts by weight | 50 parts by weight |
| 1-Menthol | | 3 parts by weight |

EXAMPLE 3

The compositions for electroporation in Examples 1 and 2 above were measured of their percutaneous absorption promoting effect by a percutaneous permeability test by using a Franz cell. More particularly, to a Franz cell 1, a skin sample 2 which had been obtained from the abdominal part of a hairless rat and from which subcutaneous fat had been removed was attached as a separator with the keratin layer directed toward the donor side. The receiver side was filled with physiological saline 3 while the donor side was filled with 3 mL of the composition 4 for electroporation of the present invention. The receiver side was stirred at 1,200 rpm by a stirrer 6 by use of a star-head type stirrer 5. Each 0.3 mL aliquot was collected with passage of time, and the same amount of physiological saline was added thereto and percutaneous permeability was examined. The amount of sodium calcein was measured by using a fluorometer. As the control, physiological saline solution of 1 mM sodium calcein was used. Electroporation was conducted under the conditions of using GENE PULSER produced by BIO-RAD Co. as a pulse voltage generator 7 at 300 V at a capacitance of a capacitor of 25 μm with applying 1 pulse (0.5 minute intervals) in first 5 minutes out of 60 minutes and turning off the voltage for the remaining 55 minutes. The results are shown in Table 2 in terms of cumulative permeation amount for 6 hours (nmol/cm$^2$). From this, it can be seen that the compositions for electroporation of the present invention have excellent percutaneous absorption promoting effect. Comparing this with the case where no electroporation was performed, it is evident that such an effect is obtained as a result of a synergistic effect by a use combined with electroporation (EP). This is also conceived with respect to the effect obtained in the case where monoterpene was further added. This apparatus is shown in FIG. 1.

TABLE 2

| Sample | EP or non-EP | Six hour cumulative permeation amount |
|---|---|---|
| Control | non-EP | 2.53 |
|  | EP | 15.02 |
| Example 1 | non-EP | 0.47 |
|  | EP | 245.04 |
| Example 2 | non-EP | 28.34 |
|  | EP | 800.85 |

EXAMPLES 4 To 6

Compositions (liquid agents) for electroporation of the present invention were produced by varying the concentration of propylene glycol according to the recipes shown below. That is, the components in the recipes were stirred and solubilized to obtain compositions. These were measured for cumulative permeation amounts for 6 hours in the same manner as in Example 3. The results are shown in Table 3. From this, it can be seen that an optimal concentration exists for the polyhydric alcohol and the content of polyhydric alcohol is preferably 5 to 30% by weight.

TABLE 3

| Example | Composition (parts by weight) | | Six hour cumulative permeation amount |
|---|---|---|---|
| Example 4 | Physiological saline | 90 | 679.81 |
|  | Propylene glycol | 10 |  |
|  | sodium calcein | 1 mM |  |
| Example 5 | Physiological saline | 75 | 671.12 |
|  | Propylene glycol | 25 |  |
|  | sodium calcein | 1 mM |  |
| Example 6 | Physiological saline | 0 | 48.13 |
|  | Propylene glycol | 100 |  |
|  | sodium calcein | 1 mM |  |

EXAMPLES 7 TO 9

According to the recipes shown below, compositions for electroporation of the present invention were prepared. That is, the components in the recipes were stirred and solubilized to obtain compositions for electroporation.

| Physiological saline | 69 parts by weight |
|---|---|
| Buprenorphin hydrochloride | 1 part by weight |
| Polyhydric alcohol* | 30 parts by weight |

*Details are shown in Table 4.

TABLE 4

| Example | Polyhydric alcohol |
|---|---|
| Example 7 | 1,3-Butanediol |
| Example 8 | Diglycerol |
| Example 9 | Polyethylene glycol 200 |

EXAMPLE 10

According to the recipe shown below, a composition for electroporation of the present invention was prepared. That is, the components in the recipe were stirred and solubilized to obtain a composition for electroporation.

| Physiological saline | 69 parts by weight |
|---|---|
| Eel carcitonin | 1 part by weight |
| Propylene glycol | 30 parts by weight |

EXAMPLE 11

According to the recipe shown below, a composition for electroporation of the present invention was prepared. That is, the recipe component A was stirred, dispersed and solubilized and the recipe component B was added thereto to neutralize the mixture and obtain a composition (gel) for electroporation.

| A | |
|---|---|
| Physiological saline | 49 parts by weight |
| Carboxyvinyl polymer | 0.6 parts by weight |
| Buprenorphin hydrochloride | 1 part by weight |
| Propylene glycol | 30 parts by weight |
| B | |
| Physiological saline | 19 parts by weight |
| Potassium hydroxide | 0.4 parts by weight |

EXAMPLE 12

According to the recipe shown below, a composition for electroporation of the present invention was prepared. The production method was the same as in Examples 1 and 2. When examining this according to the test method in Example 3, it was revealed that it had a six hour cumulative permeation amount of 0.87 µmol/cm$^2$ when electric field was not applied to, and of 480.41 µmol/cm$^2$ when electric field was applied to. This indicates that glycerol also has excellent permeation promoting effect and such an effect can be expected for polyhydric alcohols in general.

| Physiological saline | 50 parts by weight |
|---|---|
| sodium calcein | 1 mM |
| Glycerol | 50 parts by weight |

INDUSTRIAL APPLICABILITY

According to the present invention, a composition for percutaneous administration which is suitable for electroporation can be provided and the present invention is useful in the field of drugs.

What is claimed is:

1. A drug unit assembly for external application to skin, comprising a device for electroporation in combination with a composition to be administered by electroporation, whereby the composition consists essentially of a drug, menthol and 5 to 30% by weight of polyhydric alcohol.

2. The drug unit for external application to skin according to claim 1, wherein the polyhydric alcohol is one or more selected from the group consisting of propylene glycol, glycerol, polyethylene glycol, and 1,3-butanediol.

3. The drug unit for external application to skin according to claim 1, wherein the polyhydric alcohol is propylene glycol.

4. A method for administrating a drug to a patient by electroporation comprising the steps of:

applying a composition consisting essentially of the drug, 0.1 to 5% by weight of menthol, and polyhydric alcohols to skin; and impressing electric current to the skin, thereby elevating a percutaneous absorbability of the drug to the skin and permeating the drug through the skin.

* * * * *